United States Patent [19]

Tomiya

[11] Patent Number: 5,452,080
[45] Date of Patent: Sep. 19, 1995

[54] IMAGE INSPECTION APPARATUS AND METHOD

[75] Inventor: Hiroshi Tomiya, Tokyo, Japan

[73] Assignee: Sony Corporation, Tokyo, Japan

[21] Appl. No.: 251,380

[22] Filed: May 31, 1994

[30] Foreign Application Priority Data

Jun. 4, 1993 [JP] Japan ............................. 5-160357
Oct. 29, 1993 [JP] Japan ............................. 5-294000

[51] Int. Cl.⁶ ............................................. G01B 11/24
[52] U.S. Cl. ........................................................ 356/237
[58] Field of Search ........................ 356/237, 394, 376

[56] References Cited

U.S. PATENT DOCUMENTS 5,140,643  8/1992  Izumi et al. ........................ 356/237

FOREIGN PATENT DOCUMENTS 130606  6/1991  Japan ................................. 356/237

*Primary Examiner*—Richard A. Rosenberger
*Attorney, Agent, or Firm*—Ronald P. Kananen

[57] ABSTRACT

An apparatus and method for inspecting the appearance of a semiconductor device to easily judge the acceptability of the device with a simple structure. The apparatus comprises light-reflecting means and an optical reading mechanism. The light-reflecting means is disposed alongside of at least one side surface of the semiconductor device. The reading mechanism reads an image of the side surface reflected by the light-reflecting means and an image of the top or bottom surface of the device simultaneously. The method is initiated by placing the light-reflecting means alongside of at least one side surface of the device. Then, the optical reading mechanism reads an image of the side surface reflected by the light-reflecting means and an image of the top or bottom surface of the device simultaneously. The bending of each lead of the semiconductor device is inspected according to the images read by the reading mechanism.

6 Claims, 9 Drawing Sheets ( related art )

IMAGE INSPECTION APPARATUS AND METHOD

BACKGROUND OF THE INVENTION

1. Field of the Invention

The present invention relates to an apparatus and method for inspecting the appearance of a semiconductor device having leads extending from its package, by inspecting the bending of each lead.

2. Description of the Related Art

A semiconductor device sealed by a package has leads extending from the side surfaces. These leads are trimmed and formed so that they are bent into a desired form to make gull wing leads, J leads, or other leads.

In order to examine whether the bending of each lead of the semiconductor device satisfies certain requirements, the appearance of the semiconductor device is normally inspected.

FIG. 1 is a schematic perspective view of an apparatus for inspecting the appearance of the semiconductor device, indicated by numeral 3. This semiconductor device 3 is equipped with a package 4 which has leads 5 extending from the sides. The appearance-inspecting apparatus, generally indicated by reference numeral 1, comprises an optical reading mechanism 2 consisting of a CCD image sensor, line sensor, or the like. The reading mechanism 2 is disposed at one side of the package 4 of the semiconductor device 3. An image of the leads 5 extending from the sides of the package 4 can be read by the optical reading mechanism 2.

The appearance of the semiconductor device 3 is inspected by the apparatus 1 in the manner now described. First, the optical reading mechanism 2 is placed at one side of the package 4 of the semiconductor device 3. An image of the leads 5 extending from the sides of the semiconductor device 3 is read by the optical reading mechanism 2. The bending of each lead 5 is calculated from the image of the side surface of the semiconductor device 3 read by the reading mechanism 2. Then, it is determined whether the calculated value is within a given range. In this way, the semiconductor device 3 is judged to be acceptable or not.

For example, where the package 4 consists of a quad flat package (QFP) and the leads 5 extend from the four sides of the package 4, an image of one side of the device is read. Then, the semiconductor device 3 is rotated through 90° within the plane of the top surface of the device 3, followed by reading of the next side image. Reading of this kind is repeated. In this manner, images of the four sides are obtained.

The apparatus and method for inspecting the appearance of the semiconductor device constructed as described above have the following problems. The optical reading mechanism disposed at one side of the semiconductor device can obtain only one frame of image from each one side surface of the semiconductor device. Therefore, it is necessary to obtain plural frames of image according to the number of sides from which leads extend. This complicates the processing for judging whether the semiconductor device is acceptable or not. Also, the structure of the apparatus is rendered complex.

In the inspection method using this appearance-inspecting apparatus, it is necessary to rotate the semiconductor device according to the number of the sides from which leads extend and to obtain images of the individual sides. Furthermore, it is difficult to shorten the inspection time because each different image is judged separately.

Accordingly, placement of optical reading mechanisms on the sides of all the side surfaces from which leads extend may be contemplated. This makes it unnecessary to rotate the semiconductor device but the structure of the apparatus cannot be readily simplified.

OBJECTS AND SUMMARY OF THE INVENTION

It is an object of the present invention to provide an apparatus which is simple in structure and capable of easily judging whether each individual semiconductor device is acceptable or not.

It is another object of the invention to provide a method of easily judging whether each individual semiconductor device is acceptable or not, using an apparatus that is simple in structure.

An appearance-inspecting apparatus according to the invention optically reads plural leads extending from sides of the package of a semiconductor device, the package being substantially rectangular. The apparatus has light-reflecting means located on the side of at least one side surface of the semiconductor device. The apparatus further includes an optical reading mechanism which reads an image of one side surface of the semiconductor device reflected by the light-reflecting means and an image of the top or bottom surface of the device at the same time.

Another appearance-inspecting apparatus according to the invention has a light-emitting means positioned on the side of at least one side surface of the semiconductor device. The apparatus further includes a light-reflecting means on the opposite side of this side surface to reflect light emanating from the semiconductor device. The apparatus further includes an optical reading mechanism which reads an image of the side surface of the semiconductor device and an image of the top or bottom surface of the device simultaneously. The former image is created by the light which is projected onto the device and reflected by the reflecting means. The image of the top or bottom surface of the semiconductor device may also be a projection image.

A further appearance-inspecting apparatus according to the invention has a first light-emitting means for emitting first light polarized in a first direction. This light-emitting means is positioned on the side of one side surface of a semiconductor device. The apparatus further includes a second light-emitting means for emitting second light polarized in a second direction. This second light-emitting means is located on the side of the opposite side surface. A first optical part for reflecting the first light emanating from the semiconductor device and for transmitting the second light emitted by the second light-emitting means is disposed on the side of said opposite side surface. A second optical part for reflecting the second light emanating from the semiconductor device and for transmitting the first light emitted by the first light-emitting means is disposed on the side of said one side surface.

A still other appearance-inspecting apparatus according to the invention has the same components as those of the apparatus described in the immediately preceding paragraph and further includes a first polarizing plate disposed on the side of said opposite side surface. The first light polarized in the first direction and emanating from the semiconductor device is reflected by the first optical part. This first light is then transmitted through the first polarizing plate. A second polarizing plate is disposed on the side of said one side surface. The light polarized in the second direction and emanating from the semiconductor device is reflected by the second optical part. This light is transmitted through the second polarizing plate. An optical reading mechanism is further provided. This reading mechanism accepts light rays transmitted through the first and second polarizing plates, respectively, after the rays emanate from the semiconductor device. The reading mechanism obtains projection images of the side surfaces of the semiconductor device.

This apparatus is still characterized in that a first variable polarizing means whose direction of polarization is varied by application of a voltage is mounted between the first polarizing plate and the first optical part, and that a second variable polarizing means whose direction of polarization is varied by application of a voltage is mounted between the second polarizing plate and the second optical part.

An inspection method according to the present invention is used to inspect the appearance of a semiconductor device encased in a substantially rectangular package having plural leads extending from side surfaces of the package, by optically reading the leads. The method is initiated with placing the semiconductor device in position. Light-reflecting means are placed on the side of at least one side surface of the semiconductor device. Then, an image of one side surface of the semiconductor device reflected by the reflecting means and an image of the top or bottom surface of the semiconductor device are simultaneously read by a single optical reading mechanism. The bending of each lead of the semiconductor device is inspected according to the images read as described above.

In one feature of the above method, given voltages are applied to the first and second variable polarizing means so that either light emanating from the leads or reflected light is read by the optical reading mechanism.

An image of one side surface of the package is reflected toward the optical reading mechanism by the light-reflecting means disposed on the side of this side surface of the package. The optical reading mechanism can read an image of the top or bottom surface of the semiconductor device and an image of the side surface at the same time, the latter image being reflected by the light-reflecting means.

If a light-emitting means is located on the opposite side of the light-reflecting means, light emitted by the light-emitting means is made to hit the semiconductor device, and is reflected by the light-reflecting means, then the optical reading mechanism can obtain a projection image of the side surface of the semiconductor device and an image of the top or bottom surface of the device simultaneously. By using light rays polarized in different directions, images of two opposite side surfaces of the semiconductor device can be obtained simultaneously.

An image of the top or bottom surface of the semiconductor device and an image of one side surface from which leads extend can be obtained in one frame by placing the light-reflecting means described above on the side of this side surface and reading simultaneously the image of the top or bottom surface of the semiconductor device and the image of the side surface reflected by the light-reflecting means.

The directions of polarization of light rays transmitted through the first and second variable polarizing means, respectively, are rotated by applying voltages to these polarizing means. Thus, it is possible to determine whether a projection image of the semiconductor device or a reflection image should be obtained.

Other objects and features of the invention will appear in the course of the description thereof, which follows.

DETAILED DESCRIPTION OF THE PREFERRED EMBODIMENTS

Figure 1:
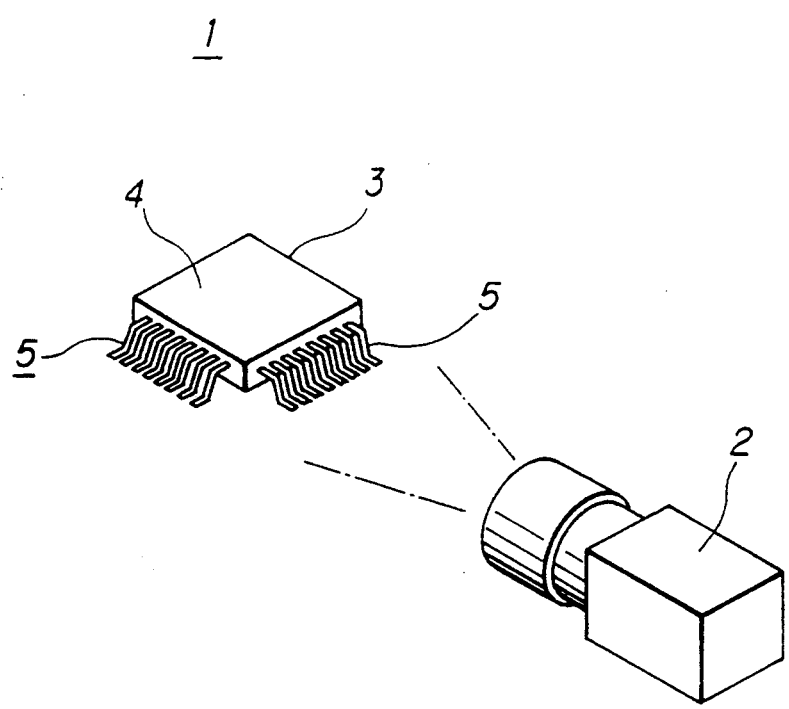
FIG. 1 is a schematic perspective view of the related art appearance-inspecting apparatus.
Figure 2:
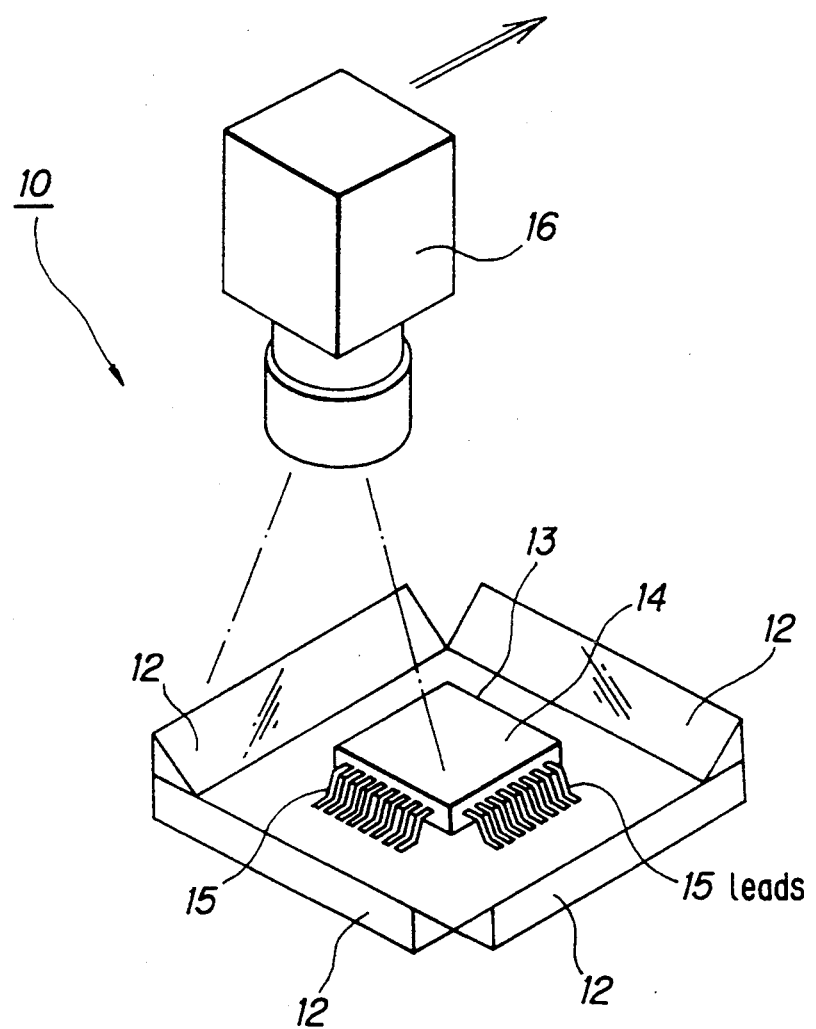
FIG. 2 is a perspective view of an appearance-inspecting apparatus, illustrating the appearance-inspecting apparatus and a method of inspection which form first and second embodiments, respectively, of the invention.

An appearance-inspecting apparatus forming first and second embodiments of the invention is first described by referring to the schematic perspective view of FIG. 2. This inspecting apparatus, generally indicated by reference numeral 10, is designed to inspect the appearance of a semiconductor device 13 encased in a package 14 having side surfaces from which leads 15 extend, by optically reading the leads 15. The apparatus 10 includes light-reflecting means 12 and an optical reading mechanism 16 which is located, for example, above the top surface of the semiconductor device 13. The light-reflecting means 12 are positioned on the side of at least one side surface of the semiconductor device 13.

For example, the light-reflecting means 12 each consist of a rectangular prism or reflecting mirror and are disposed on the sides of the side surfaces from which the leads 15 of the semiconductor device 13 extend.

The optical reading mechanism 16 is made of a CCD image sensor or line sensor and designed to read an image of the top or bottom surface of the semiconductor device 13 and an image of one side surface of the semiconductor device 13 simultaneously, the latter image being reflected by the reflecting means 12. Therefore, the frame of image obtained by the optical reading mechanism 16 contains a top view or bottom view of the semiconductor device 13 and a side view showing the side surface from which the leads 15 extend.

A method of inspecting the appearance of the semiconductor device 13 by the use of this appearance-inspecting apparatus 10 constructed as described above is now described. First, the semiconductor device 13 is placed in position. The light-reflecting means 12 are placed alongside of the side surfaces from which the leads 15 extend. The reflecting means 12 are arranged along the sides of the package 14. The reflecting surfaces of the reflecting means 12 are inclined at about 45 degrees. Where the semiconductor device 13 comprises a quad flat package, the light-reflecting means 12 are disposed on all the sides of the four side surfaces of the semiconductor device 13.

Then, the optical reading mechanism 16 consisting of a CCD image sensor or line sensor is placed, for example, above the top surface, of the semiconductor device 13. That is, the reading mechanism 16 is located on the side of the top surface of the semiconductor device in a position where this mechanism can view the reflecting surfaces of the light-reflecting means 12.

The optical reading mechanism 16 reads an image of the top surface of the semiconductor device 13 (i.e., a top view) and an image of one side surface of the semiconductor device 13 (i.e., a side view) simultaneously, the latter image being incident on the reading mechanism via the light-reflecting means 12.

Where the optical reading mechanism 16 is made of a line sensor, the reading mechanism 16 is moved parallel to the top surface consisting of a major flat surface as indicated by the arrow to read the whole image of the semiconductor device 13.

Figure 3:
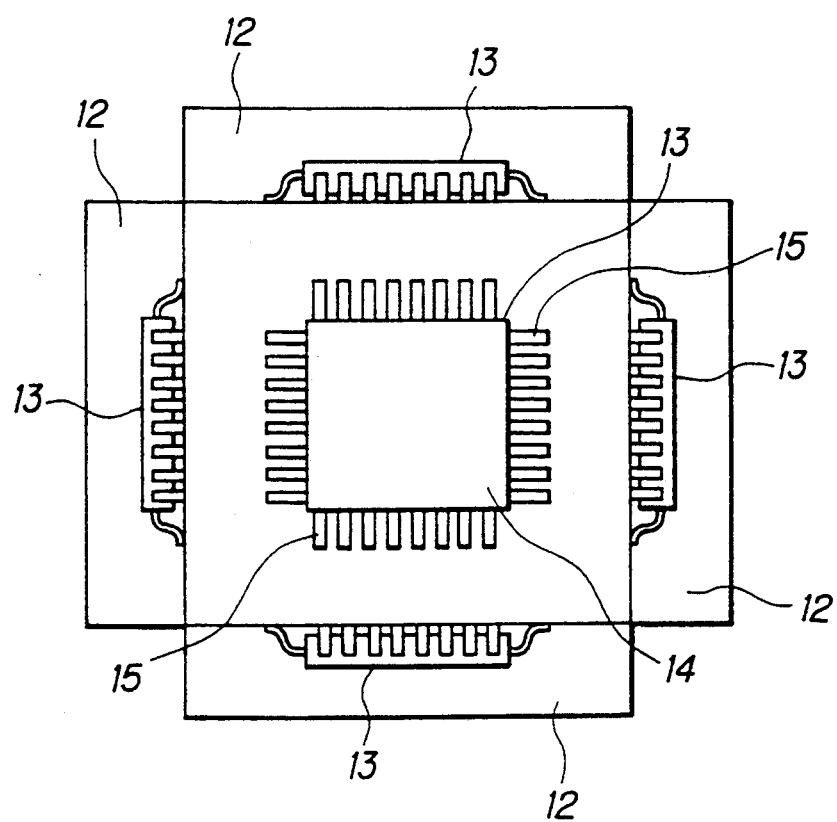
FIG. 3 is a view illustrating a frame of image that is read by the optical reading mechanism of the apparatus shown in FIG. 2.

FIG. 3 shows a frame of image read by the optical reading mechanism 16. This frame of image contains both a direct image of the top surface of the semiconductor device 13 (i.e., a top view) and an image of one side surface of the semiconductor device 13 (i.e., a side view), the latter image being incident on the reading mechanism via the light-reflecting means 12. The bending of each lead 15 extending from the side surface is judged according to the frame of image read in this way. Also, the bending of each lead 15 as viewed from above the top surface of the package is judged.

Figure 4A:
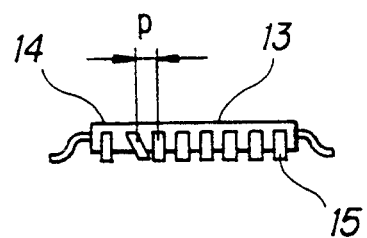
FIGS. 4A, 4B, and 4C are views, illustrating three kinds of bending of leads, i.e., lead pitch, coplanarity, and the manner in which the leads extend, respectively.
Figure 4B:
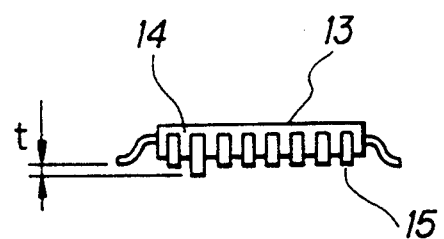
Figure 4C:
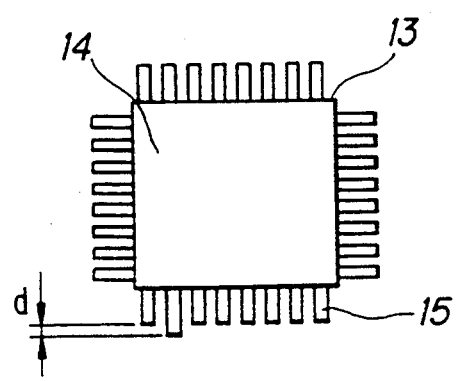

FIGS. 4A, 4B, and 4C illustrate three kinds of bending of each lead 15 which are items to be inspected. FIG. 4A illustrates the lead pitch. FIG. 4B illustrates the coplanarity. FIG. 4C illustrates the manner in which the leads extend.

Where the lead pitch p illustrated in FIG. 4A is inspected, the pitch between the successive leads 15 is measured from the image of the side surface of the semiconductor device 13 contained in the frame of image, the former image being obtained via the light-reflecting means 12. The measured pitch p is judged whether it lies within a predetermined range. Thus, a decision is made as to whether the lead pitch of the semiconductor device 13 is good or not.

Where the acceptability of the coplanarity illustrated in FIG. 4B is inspected, the same frame of image (FIG. 3) as the aforementioned frame of image used to inspect the lead pitch is used. The length t of the protrusion of the longest lead 15 is measured from the image of the side surface of the semiconductor device 13. A decision is made as to whether this length lies within a predetermined range. The acceptability of the coplanarity of the semiconductor device 13 is judged according to the result of this decision.

The frame of image read by the reading mechanism as shown in FIG. 3 contains the image of the top surface of the semiconductor device 13 (i.e., a top view) as well as the image of the side surface of the semiconductor device 13 (i.e., a side view) used in the inspections of the lead pitch and the coplanarity. Therefore, a decision can be made as to whether the leads of the semiconductor device 13 shown in FIG. 4C extend properly. That is, the distance that the longest lead 15 extends from the side surface of the package 14 is measured from the image of the top surface of the semiconductor device 13. For example, this distance is a deviation d from a reference value. A decision is made according to this deviation as to whether the lead extends properly. In this way, various kinds of bending of leads can be inspected from one read frame of image as shown in FIG. 3.

Figure 5:
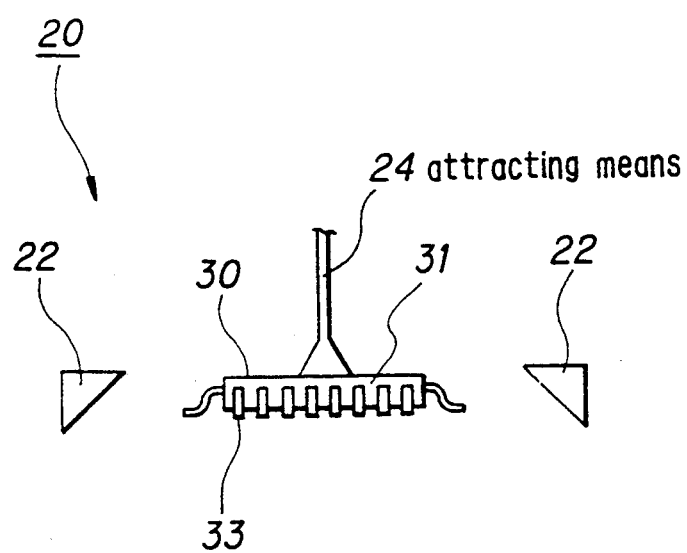
FIG. 5 is a schematic view of a third embodiment of the invention.
Figure 5:
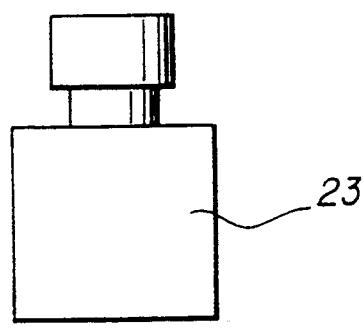

A third embodiment of the invention is next described by referring to the schematic view of FIG. 5. This appearance-inspecting apparatus, generally indicated by reference numeral 20, has light-reflecting means 22 which are disposed alongside of the side surfaces of a semiconductor device 30. An optical reading mechanism 23 is mounted under the bottom surface of the semiconductor device 30. Therefore, the reflecting surfaces of the light-reflecting means 22 face the optical reading mechanism 23 which is located under the bottom surface of the semiconductor device 30.

When the appearance of the semiconductor device 30 is inspected, using this apparatus 20, the top surface of the semiconductor device 30 is attracted and held to an attracting means 24 such as a vacuum chuck and placed among the light-reflecting means 22.

Under this condition, the optical reading mechanism 23 reads an image of the bottom surface of the semiconductor device 30 (i.e., a bottom view) and an image of one side surface of the semiconductor device 30 (i.e., a side view) simultaneously, the latter image being obtained via the light-reflecting means 22. Based on these images, the aforementioned various kinds of bending of leads are inspected and their acceptability is judged.

The top surface of the semiconductor device 30 can be attracted and held by the attracting means 24 by placing the optical reading mechanism 23 under the bottom surface of the semiconductor device 30. With an ordinary conveyor line, the top surface of the semiconductor device 30 is often attracted to hold the device. Therefore, the bending of each lead can be inspected without the need to disconnect the semiconductor device 30 from the attracting means 24.

Since the semiconductor device 30 is suspended in this way, if the acceptability of the coplanarity as shown in FIG. 4B is judged, a reference line, or a so-called seating plane, under the condition in which the semiconductor device 30 is grounded is calculated from the image of the side surface of the semiconductor device 30, the image being contained in the frame of image obtained (FIG. 3). Then, the length t of the protrusion of the longest lead 15 from this seating plane is calculated.

In the appearance-inspecting apparatus 20 and appearance inspection method described thus far, reflected light forming an image of one side surface of the semiconductor device 30 is received by the optical reading mechanism 23. In this method, however, there is a possibility that light reflected by the end surface of each lead 33 is received by the reading mechanism. If the image read contains the light reflected by the end surface, then image processing such as processing to express the image in terms of binary digits is adversely affected. This causes errors in various measurements and detections.

Figure 6:
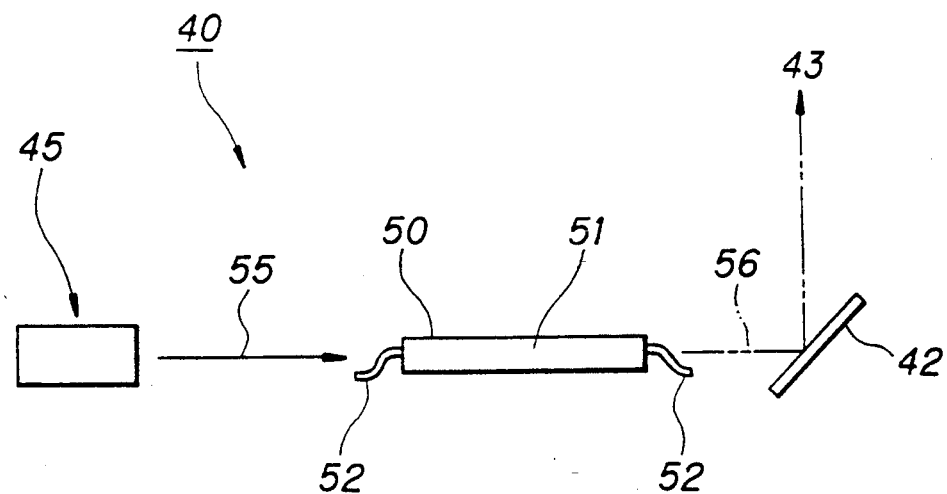
FIG. 6 is a schematic view of a fourth embodiment of the invention.

A fourth embodiment of the invention is intended to solve this drawback. This fourth embodiment is now described by referring to FIGS. 6 and 7. An appearance-inspecting apparatus 40 shown in the schematic view of FIG. 6 consists principally of a light-emitting means 45 such as a light-emitting diode and a light-reflecting means 42. The light-emitting means 45 is disposed alongside of at least one side surface of a semiconductor device 50. The light-reflecting means 42 is disposed alongside of the opposite side surface.

In this appearance-inspecting apparatus 40, light emitted by the light-emitting means 45 is projected onto one side surface of the semiconductor device 50. Projection light 56 emanating from the side surface is reflected, for example upward, by the light-reflecting means 42 disposed on the side of the opposite side surface.

This projection light 56 is received by an optical reading mechanism 43 to obtain projection images of the package 51 and the leads 52 of the semiconductor device 50.

Figure 7:
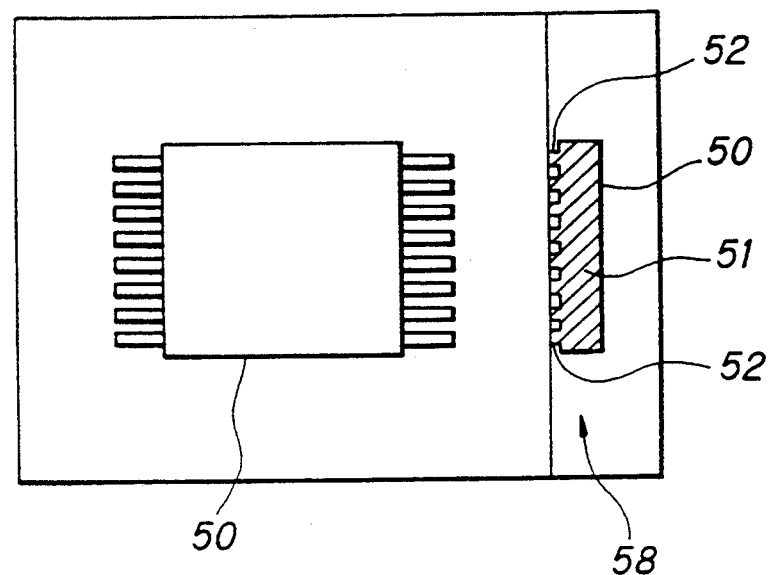
FIG. 7 is a view illustrating a frame of image read by the fourth embodiment shown in FIG. 6.

FIG. 7 shows a frame of an image received by the optical reading mechanism 43. This received image frame contains both an image of the top surface of the semiconductor device 50 (i.e., a top view) and a projection image of one side surface (i.e., a side view). The bending of the leads 52 is inspected according to these images.

The projection image of one side surface of the semiconductor device 50 does not contain the light reflected by the end surface of each lead 52. The profiles of the package 51 and of the leads 52 are imaged as shadows as indicated by the hatching. Consequently, signal processing such as processing to express the images in terms of binary digits is easy to perform. The bending of the leads 52 can be easily judged.

Alternatively, light may be projected from under the semiconductor device 50, and the optical reading mechanism 43 may read a projection image of the top surface of the semiconductor device 50.

This appearance-inspecting apparatus 40 is effective where one side surface of the semiconductor device 50 is inspected or where one side surface and a side surface perpendicular to it are inspected.

Figure 8:
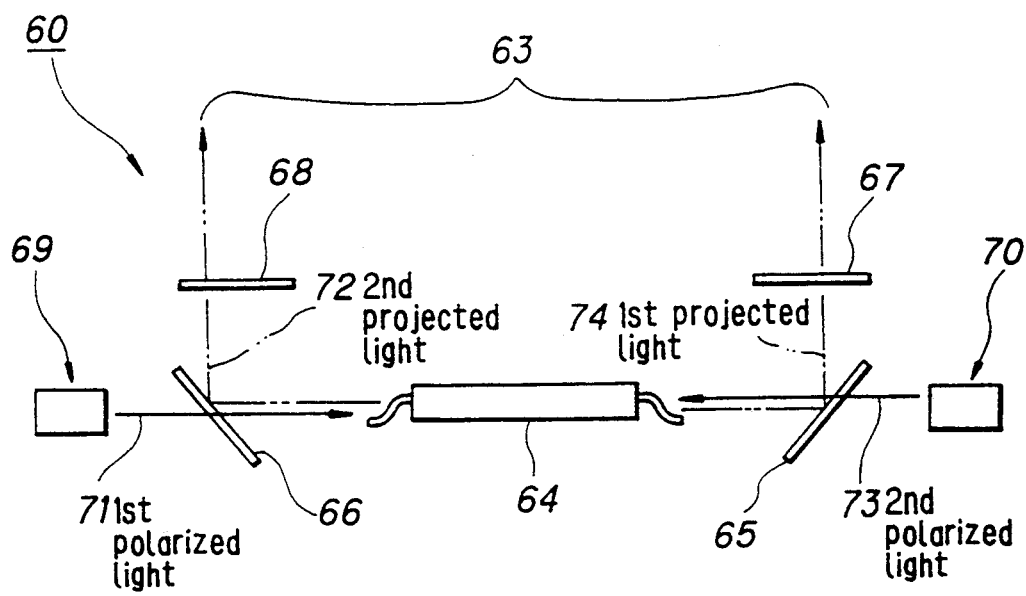
FIG. 8 is a ray diagram of a fifth embodiment of the invention.
Figure 9:
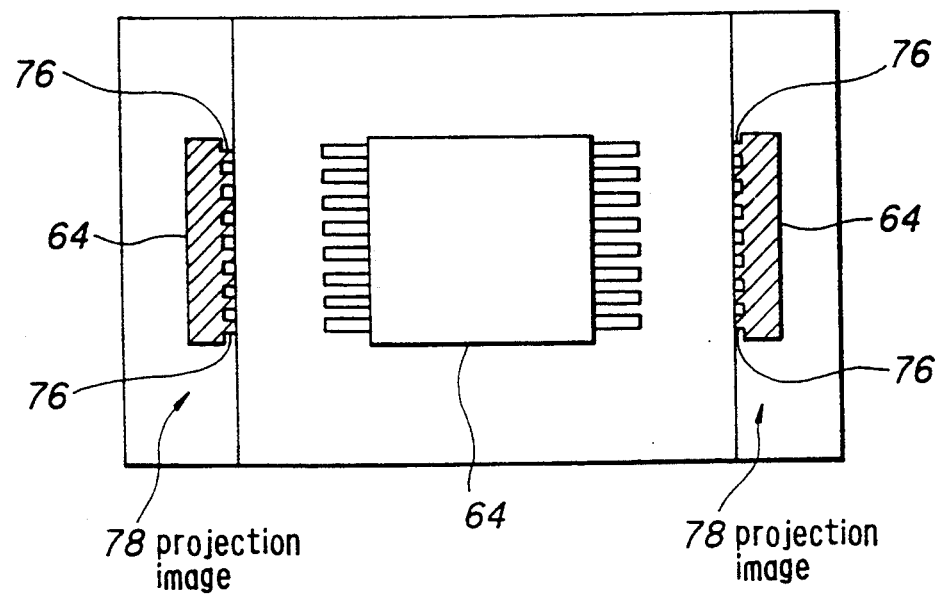
FIG. 9 is a view illustrating a frame of image read by the fifth embodiment shown in FIG. 8.

A fifth embodiment of the invention is next described by referring to FIGS. 8 and 9. An appearance-inspecting apparatus 60 shown in the schematic view of FIG. 8 consists mainly of a first light-emitting means 69 disposed alongside alongside surface of a semiconductor device 64, a second light-emitting means 70 disposed the side of the opposite side surface, a first optical part 65 disposed alongside of said opposite side surface, a second optical part 66 disposed on the side of said one side surface, a first polarizing plate 67 disposed on the side of said opposite surface, and a second polarizing plate 68 disposed on the side of said one side surface.

The first light-emitting means 69 disposed as described above emits light polarized in a first direction. This light is passed through the second optical part 66 made up of a half-mirror, a beam splitter, etc. The light then impinges on one side surface of the semiconductor device 64.

The first light polarized in the first direction is directed to one side surface. Thus, this light projected onto the semiconductor device 64 is made to hit the first optical part 65 consisting of a half-mirror, a beam splitter, etc. Then, the light is reflected, for example upward.

The first light polarized in the first direction which is reflected by the first optical part 65 is received by an optical reading mechanism 63 via the first polarizing plate 67 which can transmit only light polarized in the first direction. The second light-emitting means 70 emits second light polarized in a second direction different from the first direction of the polarization of the light emitted by the first light-emitting means 69. This second light is projected onto the opposite side surface of the semiconductor device 64. The second light then his the second optical part 66 and is reflected, for example upward. The second light reflected by the second optical part 66 is accepted by the optical reading mechanism 63 via the second polarizing plate 68 which can transmit only light polarized in the second direction.

That is, the direction of polarization of the light emitted by the first light-emitting means 69 is made coincident with the direction of polarization of the first polarizing plate 67. The direction of polarization of the light emitted by the second light-emitting means 70 is made coincident with the direction of polarization of the second polarizing plate 68. In this way, the light rays emanating from the two parallel side surfaces of the semiconductor device 64 are read by the optical reading mechanism 63.

The light 71 polarized in the first direction emitted by the first light-emitting means 69 hits one side surface of the semiconductor device 64 and is reflected upward by the second optical part 66. Since this light cannot be transmitted through the second polarizing plate 68, this light is not accepted by the optical reading mechanism 63.

Similarly, the second polarized light 73 emitted by the second light-emitting means 70 hits the other side surface of the semiconductor device 64 and is reflected upward by the first optical part 65. However, this second light is not accepted by the optical reading mechanism 63 because the light cannot be transmitted through the first polarizing plate 67. Therefore, the projected light rays can be received without being hindered by the reflected light rays.

The frame of image created by the optical reading mechanism contains an image of the top surface of the semiconductor device 64 (i.e., a top view) and images (indicated by the hatching) (i.e., side views) projected from both side surfaces, as shown in FIG. 9. The bending of each lead 76 extending from the semiconductor device 64 is inspected from the images projected from both side surfaces.

Where reflection images from side surfaces should be obtained, the first polarizing plate 67 and the second polarizing plate 68 shown in FIG. 8 are interchanged to reverse their directions of polarization. In particular, the first polarizing plate 67 does not transmit the first light reflected by the first optical part 65 but transmits the second light which hits the other side surface after being emitted from the second light-emitting means 70.

The second polarizing plate 68 transmits only light which is reflected by side surfaces after being emitted by the first light-emitting means 69. This permits the optical reading mechanism 63 to receive light rays reflected by the side surfaces of the semiconductor device 64.

A sixth embodiment of the invention is next described by referring to FIGS. 10A, 10B, 11A, and 11B. This appearance-inspecting apparatus, indicated generally by numeral 80, includes elements corresponding to the first polarizing plate 67 and the first optical part 65, respectively, of the appearance-inspecting apparatus 60 of the previously described embodiment. A first variable polarizing means 82 whose direction of polarization is varied by application of a voltage such as a liquid crystal is mounted between the first polarizing plate 86 and a first optical part 88. A similar second variable polarizing means 95 consisting of a liquid crystal or the like is mounted between a second polarizing plate 87 and a second optical part 89.

Figure 10A:
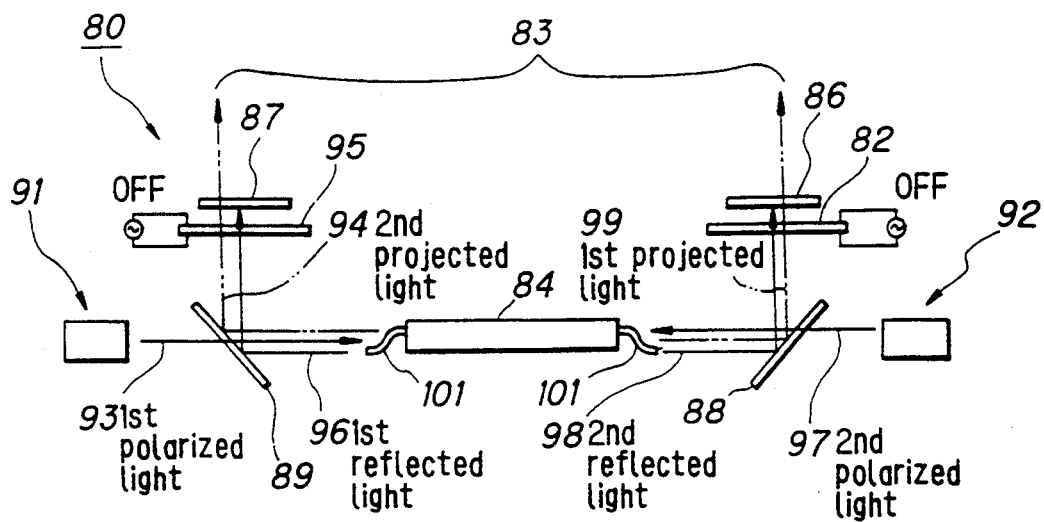
FIG. 10A is a ray diagram of a sixth embodiment of the invention, and in which projected light is accepted.

When given voltages are not applied to the first variable polarizing means 82 and the second variable polarizing means 95 as shown in FIG. 10A, i.e., when the apparatus is OFF, the first direction of polarization of the light emitted by the first light-emitting means 91 is made coincident with the direction of polarization of the first variable polarizing means 82. Also, the direction of polarization of the second light 97 emitted by the second light-emitting means 92 is made coincident with the direction of polarization of the second variable polarizing means 95.

In this way, the light 93 polarized in the first direction is projected as first projected light 99 (or first reflected light 96) from a semiconductor device 84. Then the light is reflected by the first optical part 88 and passed through the first variable polarizing means 82. The light is then transmitted through the first polarizing plate 86 in such a way that the direction of polarization is not varied.

Figure 11A:
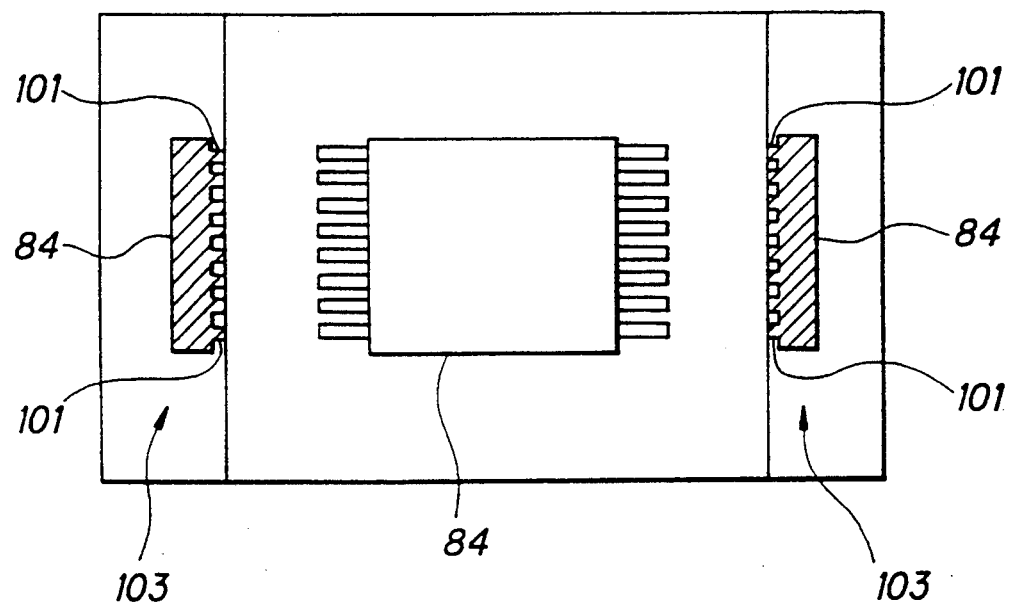
FIG. 11A is a view showing a frame of image read by the sixth embodiment, and in which the frame of image contains a projection image.

The second polarized light 97 produces the projected light 94 from the semiconductor device 84. The light is then reflected by the second optical part 89 and passed through the second variable polarizing means 95. The light is then transmitted through the second polarizing plate 87 in such a way that the direction of polarization is not varied. These projected light rays are received by the optical reading mechanism 83. As a result, projection images 102 as shown in FIG. 11A are obtained.

First reflected light 96 is reflected by the second optical part 89 and transmitted through the second variable polarizing means 95 but is blocked by the second polarizing plate 87. Second reflected light 98 is reflected by the first optical part 88 and transmitted through the first variable polarizing means 82 but blocked by the first polarizing plate 86 and so none of these light rays are received by the optical reading mechanism 83.

Figure 10B:
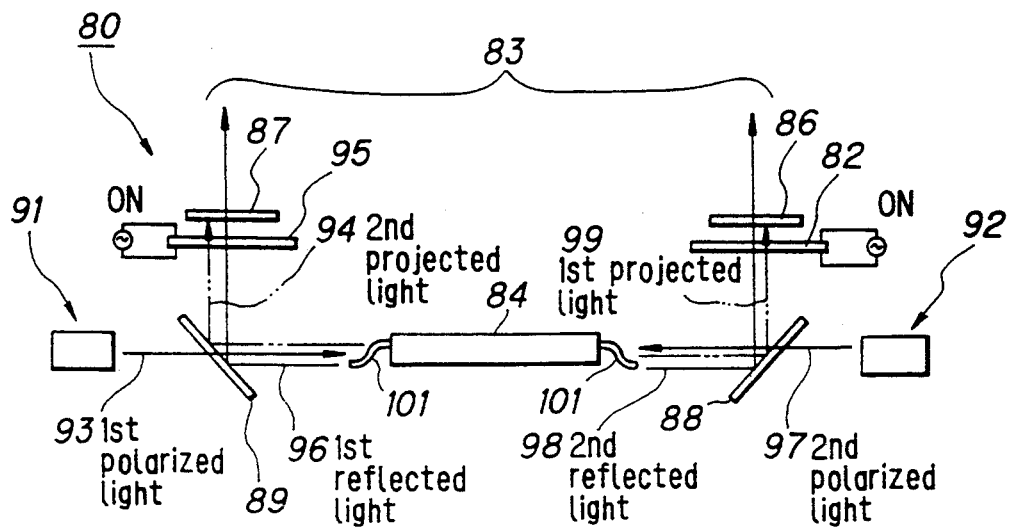
FIG. 10B is a ray diagram similar to FIG. 10A, but in which reflected light is received.

When the given voltages are applied to the first variable polarizing means 82 and the second variable polarizing means 95 as shown in FIG. 10B, i.e., when the apparatus is ON, the first and second variable polarizing means 82 and 95, respectively, rotate the direction of polarization passing through them through angles corresponding to the applied voltages. That is, the first projected light 99 passing through the first variable polarizing means 82 is rotated to the second direction of polarization by applying the given voltage to the first variable polarizing means 82. The second projected light 94 passing through the second variable polarizing means 95, is rotated to the first direction of polarization by applying the given voltage to the second polarizing means 95.

In this way, the first reflected light having the first direction of polarization, emitted by the first light-emitting means 91 is reflected by the second optical part 89 and transmitted through the second variable polarizing means 95. At this time, the direction of polarization of the first reflected light is rotated to the second direction of polarization by the second variable polarizing means 95. Therefore, this light is transmitted through the second polarizing plate 87 and received by the optical reading mechanism 83.

The first projected light 99 is reflected by the first optical part 88 and transmitted through the first variable polarizing means 82. At this time, the direction of polarization is rotated to the second direction of polarization. In consequence, the light 99 cannot pass through the first polarizing plate 86.

On the other hand, light 97, polarized in the second direction, is emitted by the second light-emitting means 92 and reflected, thus producing second reflected light 98. This light is reflected by the first optical part 88 and transmitted through the first variable polarizing means 82. At this time, the direction of polarization of the second reflected light 98 is rotated to the first direction by the first variable polarizing means 82. Therefore, the light passes through the first polarizing plate 86 and is received by the optical reading mechanism 83.

Figure 11B:
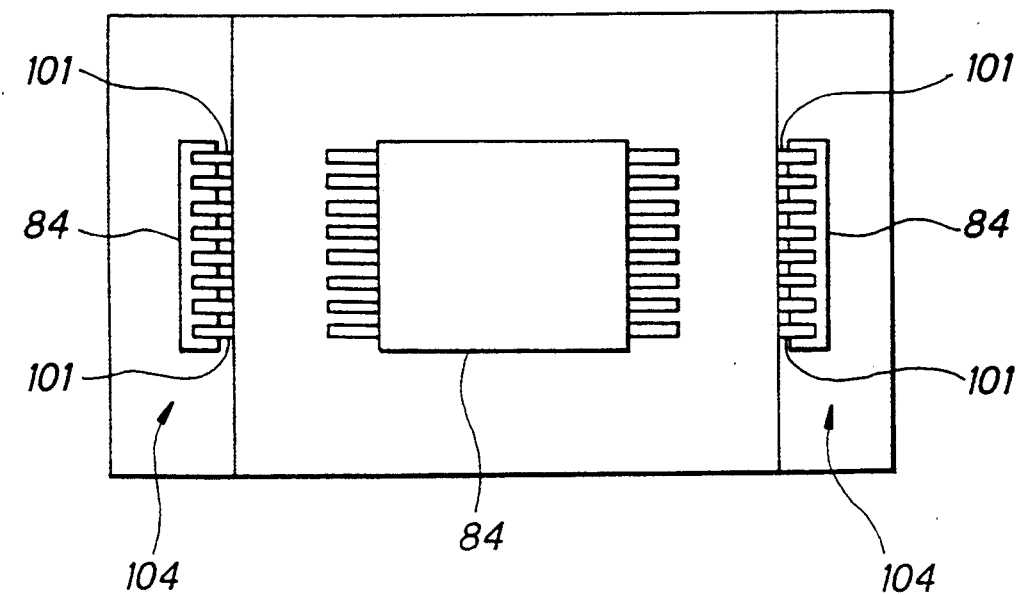
FIG. 11B is a view similar to FIG. 11A, but in which the frame of image contains a reflection image.

The second projected light 94 is reflected by the second optical part 89 and passes through the second variable polarizing means 95. At this time, the direction of polarization is rotated to the first direction and so this light cannot pass through the second polarizing plate 87. As a result, the optical reading mechanism 83 obtains a reflection image 104 of side surfaces of the semiconductor device 84 as shown in FIG. 11B.

In this way, the obtained image can be electrically switched between the projection image of side surfaces of the semiconductor device 84 and the reflection image according to the presence or absence of voltages applied to the first variable polarizing plate 82 and the second variable polarizing plate 95.

In this example, the reflection image is derived when the voltages are impressed on the first and second variable polarizing plates 82 and 95, respectively. The directions of polarization of the two polarizing plates 86 and 87 may be so set that the projection image is obtained when the voltages are applied, contrary to the above method.

As described in the fifth and sixth embodiments, each lead 76 is measured, based principally on a projection image of side surfaces of the semiconductor device 64 or 84. A reflection image of side surfaces of the semiconductor device 64 or 84 is obtained, depending on the measured item of the lead 76 or 101 or on the shape of the semiconductor device 64 or 84 (e.g., the manner in which the lead 76 or 101 extends from the bottom surface of the package 51). In this manner, the appearance of the semiconductor device 64 or 84 can be inspected with high accuracy.

The operation of the appearance-inspecting apparatus 60 and 80 described in the fifth and sixth embodiments, respectively, is not limited to inspection of only two side surfaces of a semiconductor device 64 or 84. The apparatus may be designed to inspect all the four side surfaces.

Specifically, where the four side surfaces are inspected, a structure similar to the structure used to inspect two side surfaces is mounted opposite to the other two side surfaces. In this manner, the optical reading mechanism can obtain projection images of the four side surfaces simultaneously.

As described thus far, the novel apparatus and method for inspecting the appearance of a semiconductor device yields the following advantages. The appearance-inspecting apparatus can read a reflection image of at least one side surface of the semiconductor device and an image of the top or bottom surface simultaneously owing to the optical components such as light-reflecting means and half-mirrors disposed alongside of the side surfaces of the semiconductor device. Also, the apparatus can read a projection image of the side surfaces, an image of the top or bottom surface, and a projection image of the top or bottom surface simultaneously. This makes it unnecessary to rotate the semiconductor device. Also, it is not necessary to arrange plural optical reading mechanisms. Hence, the structure of the apparatus can be simplified greatly.

Furthermore, the obtained image can be switched between a reflection image of at least one side surface of the semiconductor device and a projection image, by making use of the difference in direction of polarization between the light rays. As a consequence, the appearance of the subject device can be inspected with higher accuracy.

In the novel appearance inspection method, the bending of each lead can be inspected according to one frame or image. Therefore, it is easy to determine whether the semiconductor device is good or defective. The inspection time can be shortened.

Especially, where the appearance of a semiconductor device encased in a package having side surfaces from which plural leads extend such as a quad flat package is being inspected, the inspection time can be shortened greatly. Also, productivity can be improved.

What is claimed is:

1. An apparatus for inspecting an electronic device having a substantially rectangular package including side surfaces from which plural leads extend, by optically inspecting said leads, said apparatus comprising:
   a first light-emitting means for emitting first light polarized in a first direction, said first light-emitting means being disposed alongside of a first of said side surfaces of said electronic device;
   a second light-emitting means for emitting second light polarized in a second direction different from said first direction, said second light-emitting means being disposed alongside of a second side surface, said second side surface being opposite to said first side surface;
   a first optical part disposed alongside of said second side surface for reflecting said first light and for transmitting said second light;
   a second optical part disposed alongside of said first side surface for reflecting said second light and for transmitting said first light;
   a first polarizing plate for transmitting said first light which is reflected by said first optical part;
   a second polarizing plate for transmitting said second light which is reflected by said second optical part; and
   an optical reading mechanism for receiving both light transmitted through said first polarizing plate and light transmitted through said second polarizing plate to thereby obtain projection images of the side surfaces of said electronic device.

2. An apparatus for inspecting as set forth in claim 1, further comprising:
   a first variable polarizing means disposed between said first polarizing plate and said first optical part for polarizing incident light in a direction which is varied by application of a voltage; and
   a second variable polarizing means disposed between said second polarizing plate and said second optical part for polarizing incident light in a direction which is varied by application of a voltage.

3. An apparatus for inspecting as set forth in claim 2, wherein said first optical part and said second optical parts each comprise half-mirrors.

4. An apparatus for inspecting as set forth in claim 2, wherein said first variable polarizing means and said second variable polarizing means each include means for selectively changing the direction of polarization of said first light passing therethrough from said first direction to said second direction, and for selectively changing the direction of polarization of said second light from said second direction to said first direction, whereby said optical reading mechanism selectively obtains either said projection images of the side surfaces of said electronic device or reflected images of the side surfaces of said electronic device.

5. An apparatus for inspecting as set forth in claim 1, wherein said first optical part and said second optical parts each comprise half-mirrors.

6. A method of inspecting the appearance of an electronic device having a substantially rectangular package including side surfaces from which plural leads extend, by optically inspecting said leads, said method comprising the steps of:
   placing said electronic device in a predetermined position wherein a light-reflecting means is disposed alongside of at least one of said side surfaces of said electronic device;
   simultaneously reading a projection image of said one side surface of said electronic device and an image of a top or bottom surface of said electronic device with an optical reading mechanism, the former image being reflected by said light-reflecting means before being received by said optical reading mechanism; and
   determining the condition of the leads of said electronic device according to the images read by said optical reading mechanism;
   wherein a polarizing means and a variable polarizing means is disposed between said light reflecting means and said optical reading mechanism, said variable polarizing means being responsive to a given voltage to change its direction of polarization from a first direction, opposite to the direction of polarization of said polarizing means, to a second direction which is the same as the direction of polarization of said polarizing means and wherein said given voltage is applied to said variable polarizing means so that said optical reading mechanism selectively receives projected light or reflected light.

* * * * *